(12) United States Patent
Flamant et al.

(10) Patent No.: US 10,049,176 B2
(45) Date of Patent: Aug. 14, 2018

(54) METHOD FOR DETERMINING CHARACTERISTICS OF HOLES TO BE PROVIDED THROUGH A PLATE AND CORRESPONDING PROGRAMME

(71) Applicants: CENTRE NATIONAL DE LA RECHERCHE SCIENTIFIQUE, Paris (FR); UNIVERSITE DE NANTES, Nantes (FR)

(72) Inventors: Gilles Flamant, Llo (FR); Lingai Luo, Nantes (FR); Yilin Fan, La Chapelle sur Erdre (FR); Min Wei, Nantes (FR)

(73) Assignees: CENTRE NATIONAL DE LA RECHERCHE SCIENTIFIC, Paris (FR); UNIVERSITE DE NANTES, Nantes (FR)

( * ) Notice: Subject to any disclaimer, the term of this patent is extended or adjusted under 35 U.S.C. 154(b) by 38 days.

(21) Appl. No.: 14/914,900

(22) PCT Filed: Aug. 29, 2014

(86) PCT No.: PCT/FR2014/052145
§ 371 (c)(1),
(2) Date: Feb. 26, 2016

(87) PCT Pub. No.: WO2015/028758
PCT Pub. Date: Mar. 5, 2015

(65) Prior Publication Data
US 2016/0210391 A1     Jul. 21, 2016

(30) Foreign Application Priority Data
Aug. 30, 2013 (FR) ..................... 13 58304

(51) Int. Cl.
*G06F 17/50* (2006.01)
*F28F 9/02* (2006.01)
(Continued)

(52) U.S. Cl.
CPC .......... *G06F 17/5072* (2013.01); *F28F 9/028* (2013.01); *F28F 9/0278* (2013.01);
(Continued)

(58) Field of Classification Search
CPC .. G06F 17/5072; G06F 17/5018; F28F 9/028; F28F 9/0278; G01N 15/088; G01N 30/6017
See application file for complete search history.

(56) References Cited

U.S. PATENT DOCUMENTS

| | | | | |
|---|---|---|---|---|
| 6,668,915 B1 * | 12/2003 | Materna | ................... | F28F 1/10 165/146 |
| 2005/0087767 A1 * | 4/2005 | Fitzgerald | ............ | B01J 19/0093 257/200 |

(Continued)

OTHER PUBLICATIONS

Search Report dated 2015.
(Continued)

*Primary Examiner* — Nha Nguyen
(74) *Attorney, Agent, or Firm* — Ipsilon USA, LLP

(57) ABSTRACT

The invention relates to a method of determining characteristics of orifices (O1, . . . , O9) to be made through a plate (2) positioned in a circuit (10) across the fluid passage. Said method comprises defining fluid data, the number of orifices, and for each orifice a control segment or area. The fluid flow rate through each orifice of the perforated plate is calculated, and for each orifice, the flow rate density is calculated by dividing said fluid flow rate by the associated control segment length or control area. The optimized or non-optimized nature of the orifice characteristic is determined by comparing said flow rate density with the mean flow rate density. If the difference in absolute value lies within a predetermined range of values, then the orifice characteristics are considered as being optimized. Otherwise at least one characteristic of at least some of the orifices is modified.

14 Claims, 6 Drawing Sheets

(51) Int. Cl.
*G01N 15/08* (2006.01)
*G01N 30/60* (2006.01)

(52) U.S. Cl.
CPC ....... *G01N 15/088* (2013.01); *G06F 17/5018* (2013.01); *G01N 30/6017* (2013.01)

(56) References Cited

U.S. PATENT DOCUMENTS

| | | | |
|---|---|---|---|
| 2007/0144708 A1* | 6/2007 | Tilton | F28D 5/00 165/104.31 |
| 2012/0111535 A1* | 5/2012 | Jukkola | F28C 3/14 165/104.18 |

OTHER PUBLICATIONS

Wang et al: "Effects of distribution channel dimensions on flow distribution and pressure drop in a plate-fin heat exchanger" Dated: Mar. 7, 2013.

Wen J et al.: "Study of flow distribution and its improvement on the header of plate-fin heat exchanger" Dated: Nov. 2004.

* cited by examiner

METHOD FOR DETERMINING CHARACTERISTICS OF HOLES TO BE PROVIDED THROUGH A PLATE AND CORRESPONDING PROGRAMME

RELATED APPLICATIONS

This application is a National Phase Application of PCT/FR2014/052145, filed on Aug. 29, 2014, which in turn claims the benefit of priority from French Patent Application No. 13 58304 filed on Aug. 30, 2013, the entirety of which are incorporated herein by reference.

BACKGROUND

Field of the Invention

The present invention relates in general manner to distributing fluid in a circuit.

Description of Related Art

In order to operate well, equipment having a circuit that passes a fluid needs to have the fluid properly distributed in said circuit. In particular, in a heat exchanger that comprises two transfer circuits passing two distinct fluids, and arranged relative to each other so as to transfer heat from the fluid flowing in one of the transfer circuits to the fluid flowing in the other transfer circuit, a poor distribution or share of fluid in one and/or the other of said circuits has the consequence of reducing the performance of said heat exchanger, and possibly of leading to hot points and/or short circuits. There is also a risk of said heat exchanger being damaged.

In the state of the art, and in particular in the document by C. Wen et al., entitled "Study of flow distribution and its improvement on the header of plate-fin heat exchanger", it is known to introduce a perforated plate across the fluid flow passage of the circuit in order to attempt to improve the uniformity with which the fluid is distributed in the circuit downstream from the plate. Nevertheless, the characteristics, of the orifices are selected empirically for each circuit shape, which does not make it possible to obtain uniformity of fluid stream distribution in reliable and repeatable manner from one circuit shape to another, or from one operating point to another. Furthermore, numerous tests are needed and such a process presents a cost that is high, effectiveness that is poor, and takes a very long time.

Also known in the state of the art is the document by W. Wang et al. entitled "Effects of distribution channel dimensions on flow distribution and pressure drop in a plate-fin heat exchanger", which provides a step of modifying the width of the outlet channels of a circuit, which is onerous and not optimized. That document does not make provision for inserting a perforated plate across the fluid flow passage of the circuit.

OBJECTS AND SUMMARY

An object of the present invention is to provide a method of determining the characteristics of orifices to be made in a plate in order to be able to obtain better uniformity in the distribution of fluid downstream from the perforated plate in a manner that is fast and reliable, and that is applicable to various different circuit designs and different working conditions.

Another object of the invention is also to be able to design a circuit that includes a plate that is made using said method, and of size that is limited with limited head loss for the fluid passing through the plate.

To this end, the invention provides a method of determining characteristics of orifices for making through a plate, said plate being for positioning in a circuit across the fluid passage, said method being characterized in that it comprises the following steps:

a) preferably, defining operational data of the circuit, which data comprises: the temperature of the fluid; and/or the pressure of the fluid; and/or the received heat flux; and/or gravity;

b) defining fluid data, including the flow rate entering the circuit, written Q, and preferably the viscosity, and/or the compressibility, and/or the density of said fluid, as a function of the temperature of the fluid and/or the pressure of the fluid;

c) defining characteristics relating to the orifices, said characteristics comprising:
the number of orifices, written N;
for each orifice:
either a segment referred to as a "control segment" of length written $L^*_i$;
or an area referred to as a "control area", written $S^*_i$;
each control segment or area corresponding to subdividing at least a portion of the length written L, of the plate or of the area, written S, of the plate such that the control segments or areas preferably join one another and contain the corresponding orifice;
the diameter, written $d_i$, or the area, written $a_i$, of the fluid passage of each orifice;

d) meshing said circuit of the plate with the corresponding orifices, together with one or more other elements, if any, present inside said circuit;

e) determining the speed of the fluid stream in a plurality of meshes, preferably in each mesh, as a function of said fluid data, and preferably of said operational data of the circuit;

f) calculating the fluid flow rate $Q_i$ through each orifice in the plate at least as a function of the diameter $d_i$ or of the area $a_i$ of said orifice, and of the determined speed of the fluid stream at said orifice;

g) calculating for each orifice the flow rate density, written $Qs_i$, by dividing the fluid flow rate $Q_i$ by the length $L^*_i$ of the control segment or by the control area $S^*_i$ associated with said orifice, and calculating the mean flow rate density, written $\overline{Q_s}$, corresponding to the ratio of the incoming flow rate Q over the length L or the area S of the plate; and h) determining the optimum or non-optimum nature of the characteristics of the orifices of the plate, by:
for each orifice, comparing the flow rate density $Qs_i$ with the mean flow rate density $\overline{Q_s}$; and
if, for each orifice, the difference in absolute value between the flow rate density $Qs_i$ and the mean flow rate density $\overline{Q_s}$ in a predetermined range of values, then the characteristics of the orifices are considered as being optimized; and
otherwise:
modifying at least one of said characteristics of at least some of the orifices; and
repeating steps d) to h).

Such a method of the invention makes it possible to optimize the distribution of fluid through a perforated plate placed across a fluid passage in a fluid flow circuit with a distribution that is more uniform or homogeneous across a flow section of the circuit downstream from the perforated plate.

The flow section that is fed with fluid downstream from the plate is formed in three dimensions (3D) by a surface and it may be reduced to a line for performing calculation in two dimensions (2D) as described in detail below.

More precisely, by choosing the flow rate density as a parameter, i.e. the flow rate relative to the control length or area, representative of the positions of the orifices relative to one another, and by comparing the flow rate density of each orifice with the mean flow rate density by associating the value of the flow rate density of each orifice with the value of the mean flow rate density, it is possible to obtain a distribution that is more uniform, in particular for the speeds of the fluid downstream from the perforated plate, thereby improving the efficiency of the installation and reducing any risk of the installation being damaged.

Depending on the type of equipment in which said circuit is installed, the space or domain of the circuit fed with fluid downstream from the perforated plate may be used to perform a function such as: heat exchange; chemical reaction; or fluid separation.

Thus, this space or domain downstream from the plate may comprise:
- a bundle of parallel tubes forming part of a heat exchanger;
- a monolithic catalyst;
- a chromatography column;
- an ion exchange column;
- a solar receiver or reactor;
- a boiler;
- a distillation; or
- a column filled with packing when a plurality of fluids are concerned.

According to an advantageous characteristic of the invention, the diameter $d_i$ of the area $a_i$ of the fluid passage of the orifice is modified to increase the diameter $d_i$ of the orifice if the flow rate density $Q_{si}$ of the orifice is less than the mean flow rate density $\overline{Q}_s$, and vice versa.

Advantageously, said at least one modified characteristic of at least some of the orifices is the diameter $d_i$ or the area $a_i$ of the fluid passage of the orifice.

According to an advantageous characteristic of the invention, said at least one modified characteristic of at least some of the orifices is the number N of orifices.

Increasing the number of orifices, possibly after changing their diameter, serves to refine the uniformity of the distribution downstream from the plate.

According to an advantageous characteristic of the invention, said at least one modified characteristic of at least some of the orifices is the length $L^*_i$ of the segment or the control area $S^*_1$ of the orifice, without the constraint of being equal to the segment length $L^*_i$ of the control area $S^*_i$ of the other orifices.

Changing the length $L^*_i$ of the segment or the control area $S^*_i$ of the orifice independently of the other orifices serves to modify the position of said orifice relative to the other orifices.

According to an advantageous characteristic of the invention, the length $L^*_i$ of each control segment, or each control area $S^*_i$, is defined as being equal to the length of each of the other segments, or equal to each of the other control areas.

According to an advantageous characteristic of the invention, the step of modifying at least one characteristic of at least some of the orifices is performed while conserving a constant porosity value for the plate, said plate porosity being defined as the sum of the fluid-passing diameters or areas of the orifices divided by the length, or the area, of the plate.

By working with constant plate porosity when executing a plurality of calculation cycles it is possible to increase the chances of causing the plates to converge and thus makes it possible to execute a plurality of series of calculation cycles with each series having a given porosity value and a given orifice configuration so as subsequently to be able to select the most suitable configuration for the orifices.

According to an advantageous characteristic of the invention, the fluid-passing diameter $d_i$ or area $S_i$ of the orifice written $d_{i,t}$ or $a_{i,t}$ is modified to or in such a manner that:

$$\Delta d_{i,t+1} = \gamma d_{i,t}\left(1 - \frac{Q_{si}}{\overline{Q}_s}\right)$$

with $\Delta d_{i,t+1} = d_{i,t+1} - d_{i,t}$, and $\gamma$ being a strictly positive real coefficient; or $$\Delta a_{i,t+1} = \gamma a_{i,t}\left(1 - \frac{Q_{si}}{\overline{Q}_s}\right)$$

with $\Delta \alpha_{i,t+1} = \alpha_{i,t+1} - \alpha_{i,t}$, and $\gamma$ being a strictly positive real coefficient.

According to an advantageous characteristic of the invention, for each orifice, the diameter $d_i$ or the fluid passage $a_i$ and the length $L^*_i$ of the segment or the control area $S^*_i$ are selected in such a manner that $d_i/L^*_i$ is less than or equal to 1, or is less than or equal to 1. In particular, $d_i/L^*_i$ is less than or equal to 1, or $a_i/S^*_i$ is preferably kept less than or equal to 1 regardless of the iteration, i.e. regardless of the calculation cycle.

By maintaining such a constraint in the ratio of the diameter $d_i$ or the fluid passage $a_i$ and the length $L^*_i$ of the segment or the control area $S^*_i$, it is possible to improve the uniformity of speeds downstream from the plate by limiting interaction of the fluid passing through an orifice relative to the fluid passing through neighboring orifices.

According to an advantageous characteristic of the invention, the steps d) to h) correspond to a calculation cycle, the method comprising executing a first series, of calculation cycles, with a characteristic of at least some of the orifices being modified in step h), and a second series of calculation cycles being executed with another characteristic of at least some of the orifices being modified in step h).

According to an advantageous characteristic of the invention, each plurality of cycles is performed with a constant value for plate porosity from one cycle to another in the same series, but with a different value for plate porosity from one series to another.

According to an advantageous characteristic of the invention, the method comprises:
- executing a first series of calculation cycles until the defined characteristics of the orifices are considered as being optimized; and
- executing the second series, of calculation cycles until the defined characteristics of the orifices are considered as being optimized;
- for each of said series of calculation cycles, calculating the head loss associated with the orifice characteristics that are considered as being optimized; and from the orifice characteristics that are considered as being optimized, corresponding to each series of calculation cycles, selecting the series for the head loss is the smallest.

According to an advantageous characteristic of the invention, steps d) to h) correspond to a calculation cycle, and a series of calculation cycles is performed with a plate of given shape and/or size, and a second series of calculation is performed with another plate shape and/or size.

The invention also provides a computer program comprising program code instructions for executing steps of the method as described above when said program is executed on a computer.

BRIEF DESCRIPTION OF THE DRAWINGS

The invention can be better understood on reading the following description of embodiments given with reference to the accompanying drawings, in which.

DETAILED DESCRIPTION

Figure 1:
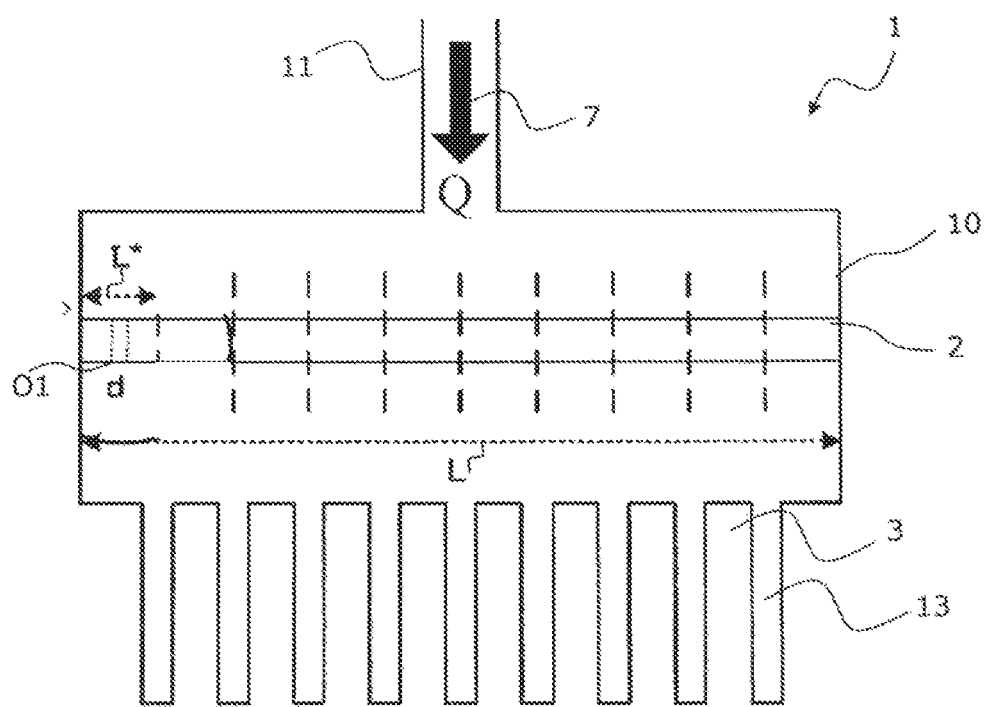
FIG. 1 is a diagrammatic view in two dimensions of a circuit having a perforated plate placed therein, the characteristics of an orifice and of the plate suitable for use in an implementation of the invention being referenced.

With reference to the figures and as summarized above, the invention relates to a method of determining the characteristics of orifices to be made through a plate 2 that is positioned in a circuit in order to make uniform the distribution and preferably also the speeds of the fluid downstream from said plate 2.

As described in detail below, the characteristics of the orifices comprise in particular the number, the diameters, and possibly the relative positions of each of the orifices. In the example shown in the figure, there are nine such orifices referenced O1 to O9. Naturally, the number of orifices could be different, and it is written N.

Said plate 2 is positioned in the circuit 10 across the fluid passage 7 downstream from the inlet 11 of the circuit.

In the example shown in the figures, the circuit 10 forms a portion of a heat exchanger 1 and has a portion 13 forming parallel fluid ducts arranged with ducts 3 of another fluid circuit of said heat exchanger so as to enable heat to be exchanged between the fluid passing along the ducts 13 and the fluid passing along said other ducts 3.

In the description below, the characteristics of these orifices are determined for a given shape defined in two dimensions (2D). Naturally, and as described in greater detail below, the following method is also applicable to a shape that is defined in three dimensions (3D).

Figure 5:
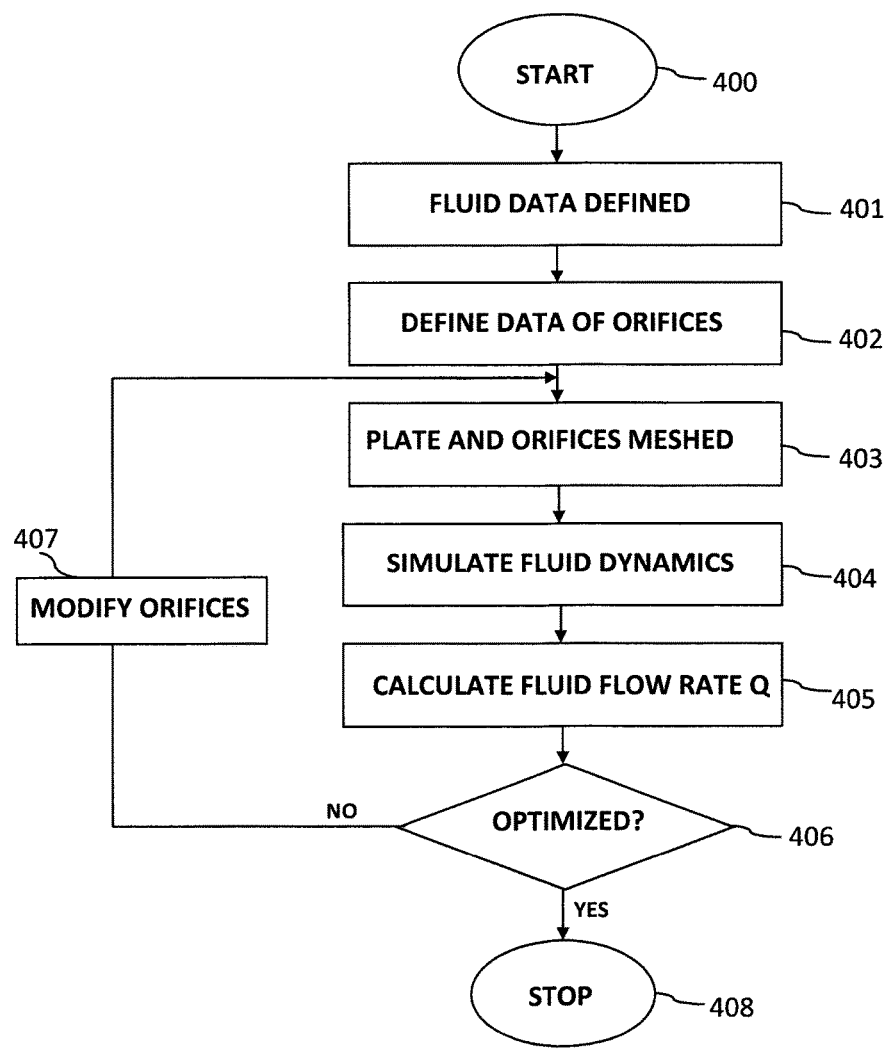
FIG. 5 is a flow chart showing the steps of an implementation of the method of the invention.

In an implementation, the method of determining the characteristics of orifices in the plate comprises the following steps, described with reference to the flow chart of FIG. 5.

At the start 400 of the method, operational data of the circuit is defined, said data advantageously comprising the temperature of the fluid, and/or the pressure of the fluid, and/or the received heat flux, and/or gravity.

In step 401, data concerning the fluid 7 entering the circuit upstream from the plate 2 is defined. This fluid data comprises the flow rate Q entering the circuit, and preferably the viscosity, and/or the compressibility, and/or the density of said fluid, as a function of the temperature of the fluid and/or of the pressure of the fluid.

Data relating to the orifices is also defined in step 402. Said characteristics, comprise the number N of orifices, and for each orifice, when using 2D geometry, there is defined a segment referred to as the control segment, which is of length $L^*_i$. Each control segment corresponds to cutting out a part or all of the length, written L, of the plate 2 such that the segments join one another and each segment includes the corresponding orifice i.

For 3D geometry, instead of defining a control segment, a control surface is defined, written $S^*_i$. Each control surface then corresponds to cutting out a part or all of the surface area, written S, of the plate 2 so that the control surfaces join one another, and each control surface surrounds the corresponding orifice i.

The control segments or surfaces are representative of the distances or areas between an orifice and another orifice, and thus of the extent of the zone immediately downstream of the plate over which the fluid will spread on leaving the corresponding orifice.

The diameter, written $d_i$, or the area, written $a_i$, of the fluid passage of each orifice is also defined. In the example shown in the figures, the diameter $d_i$ is initially identical among the orifices. In a variant, the initial diameter of each orifice may differ from one orifice to another. The same applies to the area $a_i$ of each orifice when using a 3D model.

The local porosity of art orifice, written $\varepsilon_i$, corresponds to the porosity of the plate 2 around the orifice i, with i varying from O1 to ON, with N=9 in the example shown in the figures. In 2D, the local porosity is equal to the diameter $d_i$ of the orifice over the length $L^*_i$.

The following equation can thus be defined:

$$\varepsilon_1 = \frac{d_1}{L_i^*}$$

In 3D, the local porosity is defined as above by replacing the length $L^*_i$ with the area $S^*_i$, and by replacing $d_i$ with $a_i$.

In 3D, the area $S^*_i$, which is replaced by the length $L^*_i$ in 2D, corresponds to an area around the orifice, or indeed to a control volume of the plate around the orifice if consideration is given to the thickness of the plate. In 3D, the area $a_i$, which is replaced by the diameter $d_i$ in 2D, corresponds to the fluid passage of the orifice or indeed to the volume of the orifice if consideration is given to the thickness of the plate.

When the lengths of the control segments are the same from one orifice to another, i.e. a local length $L^*$, said local length $L^*$ corresponds to the length L of the plate divided by the number of orifices, written N, present along this line length, i.e.:

$$N = \frac{L}{L^*}$$

In 2D, the ratio $d_i/L^*_i$ is selected to be less than or equal to 1. In similar manner, in 3D, the ratio $a_i/S^*_i$ is selected to be less than or equal to 1. As mentioned above, this constraint is preferably complied with regardless of the iteration for $d_i$ or $a_i$.

The overall porosity $\Phi$ of the plate is equal to the sum over i=1 to N of $d_i$ divided by the length L of the plate 2, i.e.:

$$\Phi = \frac{\sum_{i=1}^{N} d_i}{L}$$

In 3D, the porosity is defined as above, replacing the diameter $d_i$ with the fluid passage $a_i$ and the length L of the plate by the area S of the plate.

The circuit 10 and its content, in particular the plate 2 with its orifices, are meshed in step 403. The other elements 3, if any, that are present inside said circuit 10, such as the ducts 3 of the other heat exchanger circuit, are also meshed.

In particular, the outline of the circuit, its inlet and outlet, and also the inside of said circuit are meshed. It is necessary to mesh a shape in order to be able to calculate numerically the dynamic behavior of the fluid. This is a conventional technique for the person skilled in the art and is therefore not described in detail. By way of example, the meshing may be performed using the GAMBIT (registered trademark) meshing software.

The dynamic behavior of the fluid in the circuit is simulated in step 404 so as to determine the speed of the fluid flow in each mesh of the circuit as a function of the fluid data, preferably of the operational data, of the characteristics of the orifices, and of the mesh. The simulation may be performed using numerical simulation software, such as FLUENT (registered trademark) software published by the supplier ANSYS (registered trademark). The fluid speed calculation points or meshes are selected to be sufficiently numerous to be representative of the flow of fluid in each zone of the circuit.

In step 405, the fluid flow rate $Q_i$ through each orifice in the perforated plate 2 is then calculated as a function of the speed determined for the stream of fluid through each orifice, and of the diameter (2D mode) or of the fluid passage (3D mode) of said orifice. Preferably, the calculation of $Q_i$ also takes account of other physical properties of said fluid, such as its viscosity, its compressibility, and its density.

Thereafter, the flow rate density $Qs_i$ is calculated for each orifice i by dividing $Q_i$ by the control length $L^*_i$ or the control area $S^*_i$, i.e. $Qs_i = Q_i/L^*_i$ in 2D or $Qs_i = Q_i/S^*_i$ in 3D.

A mean value for flow rate density, written $\overline{Q_s}$, is defined as the ratio of the flow rate Q entering the circuit divided by the length. L of the plate (in 2D) or by the area S of the plate (in 3D).

In the particular situation of the example shown in the figures, the lengths $L^*$ are identical from one segment to another.

In step 406, for each i=1 to N, $Qs_i$ is compared with $\overline{Q_s}$ in order to determine the optimum or non-optimum nature of the characteristics of the previously defined orifices.

If the difference in absolute value between $Qs_i$ and $\overline{Q_s}$ is less than a given value, referred to as the error value, e.g. 1% or 5%, then the characteristics of the orifices are considered as being optimized and the calculation can be stopped (step 408).

Otherwise, in step 407, the diameter $d_i$ or the area $a_i$ is modified in some or all of the orifices, using the following equation in 2D:

$$\Delta d_{i,t+1} = \gamma d_{i,t}\left(1 - \frac{Q_{si}}{\overline{Q_s}}\right)$$

with $\Delta d_{i,t} = d_{i,t+1} - d_{i,t}$, and $d_{i,t}$ corresponds to the value of $d_i$ before modification and $d_{i,t+1}$ corresponds to the new value of the diameter $d_i$, i.e. the new iteration value of $d_i$ that is going to be used for relaunching the calculation; $\gamma$ being a real coefficient that is strictly positive; else, in similar manner in 3D:

$$\Delta a_{i,t+1} = \gamma a_{i,t}\left(1 - \frac{Q_{si}}{\overline{Q_s}}\right)$$

with $\Delta \alpha_{i,t+1} = \alpha_{i,t+1} = -\alpha_{i,t}$.

Using this equation to modify $d_i$ or $a_i$ as a function of the comparison of $Qs_i/\overline{Q_s}$ with the value 1 makes it possible not only to accelerate the convergence of the calculation, but also to conserve global porosity that is constant for the plate when the control segment lengths $L^*_i$ or the control areas $S^*_i$ are identical from one orifice to another.

Thereafter, calculation steps 403 to 406 are repeated until the difference in absolute value for each orifice between $Qs_i$ and $\overline{Q_s}$ is less than a given value, referred to as the error value, e.g. 1% or 5%. Preferably, calculation steps 403 to 406 are repeated while keeping overall porosity constant, at least for a given series of repetitions.

The set of steps 403 to 406 as described above is referred to as a calculation cycle in the description below.

When after a given number of iterations or calculation cycles, the difference between $Qs_i$ and $\overline{Q_s}$ remains within a predefined range of values greater than the error value, it is considered that the calculation has not converged.

In the event of non-convergence, then some other characteristic of the orifices is modified, e.g. the number N of orifices, and one or more calculation cycles are relaunched, as described above.

In general manner, provision may be made for the method to include executing a first series of calculation cycles, with a characteristic of at least some of the orifices being modified in each cycle, and then executing a second series of calculation cycles, with some other characteristic of at least some of the orifices being modified in each cycle.

Preferably, the characteristic that is modified during the first series of calculation cycles is the diameter $d_i$ (2D) or the area $a_i$ (3D) of each orifice, after which the character that is modified during the second series of calculation cycles is the number N of orifices.

Provision may also be made to modify the relative positions of the orifices in the plate by modifying the lengths of their segments or control areas relative to one another. In other words, said characteristic of the orifices that is modified may be the length $L^*_i$ of the segment or the control area $S^*_i$ of the orifice without any constraint on the segment lengths or the control areas being equal for all the orifices.

Preferably, each plurality of cycles is performed with a plate porosity value that is constant from one cycle to another in the same series, but with a plate porosity value that differs from one series to another.

In an advantageous implementation of the method of the invention, provision may be made to perform a first series of calculation cycles until the characteristics of the defined orifices are considered as being optimized, and then to perform one or more other series of calculation cycles until the characteristics of the defined orifices are also considered as being optimized. For each series, the head loss associated with the characteristics, of the orifices that are considered as being optimized is calculated, and the characteristics of the orifices that are considered as being optimized that correspond to the calculation cycle series having the smallest head loss is then selected.

After selecting the configuration of orifices that is considered as being optimized from the point of view of the uniformity of flow rates per unit area through each orifice and possibly from the point of view of head loss, the orifices can be made in the plate in compliance with said selected configuration and the plate can be put into place in the circuit of the installation at the intended position.

Figure 6:
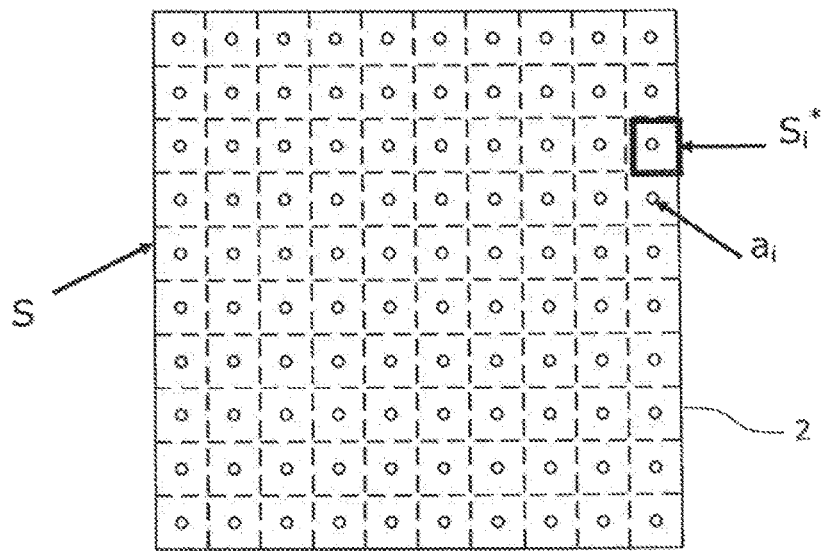
FIG. 6 is a diagrammatic view of a square plate of surface area S subdivided into control surfaces $S^*_i$ of square shape, each of which includes an orifice of fluid passage $a_i$, the characteristics of said plate being used for performing an implementation of the method of the invention, with 3D calculation.
Figure 7:
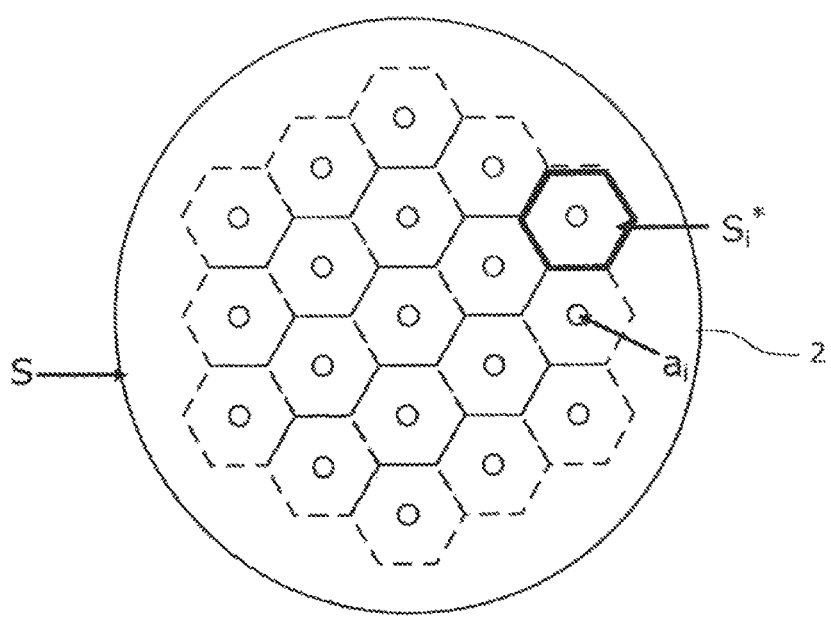
FIG. 7 is a diagrammatic view of a round plate of surface area S, having a portion subdivided into control surfaces $S^*_i$ of hexagonal shape, each including an orifice of fluid passage $a_i$, the characteristics of said plate being used for performing an implementation of the method of the invention, with 3D calculation.

In another advantageous implementation, provision may also be made to perform a series of calculation cycles with a plate of given shape and/or size (e.g. square as shown in FIG. 6), and at least one second series of calculations with a plate of some other shape and/or size (e.g. round as shown in FIG. 7).

It is thus possible to select the shape and/or size of the plate that makes it possible to obtain the best distribution of fluid. It is then possible to fabricate a plurality of plates having the shape and/or size that corresponds to at least some of the calculation series that have been performed in order to enable the operator to replace one plate with another as a function of the effects that are to be obtained.

Such an installation may be applied to separating air, to the petrochemical industry, or to other types of installation that make use of a circuit in which a fluid flows.

Such a method of optimizing the configuration of the orifices in the plate is advantageously developed in the form of an algorithm that makes it possible to obtain a distribution of fluid that is substantially uniform downstream from the plate with little increase in head loss associated with inserting the plate.

This method makes it possible to define the topology of the orifices to be drilled:
the distribution of the holes, and in particular their number, their distances, their diameters, or their fluid passages;
the shape of the holes: round; square, or other. Depending on the shape of the hole, a characteristic dimension of said hole, such as its width, may be considered as corresponding to said hole diameter used for calculation; and
the variation in the dimensions of holes as a function of their locations in the plate.

Advantageously, the steps of the above-described method are performed using program code instructions executed on a computer.

Figure 2:
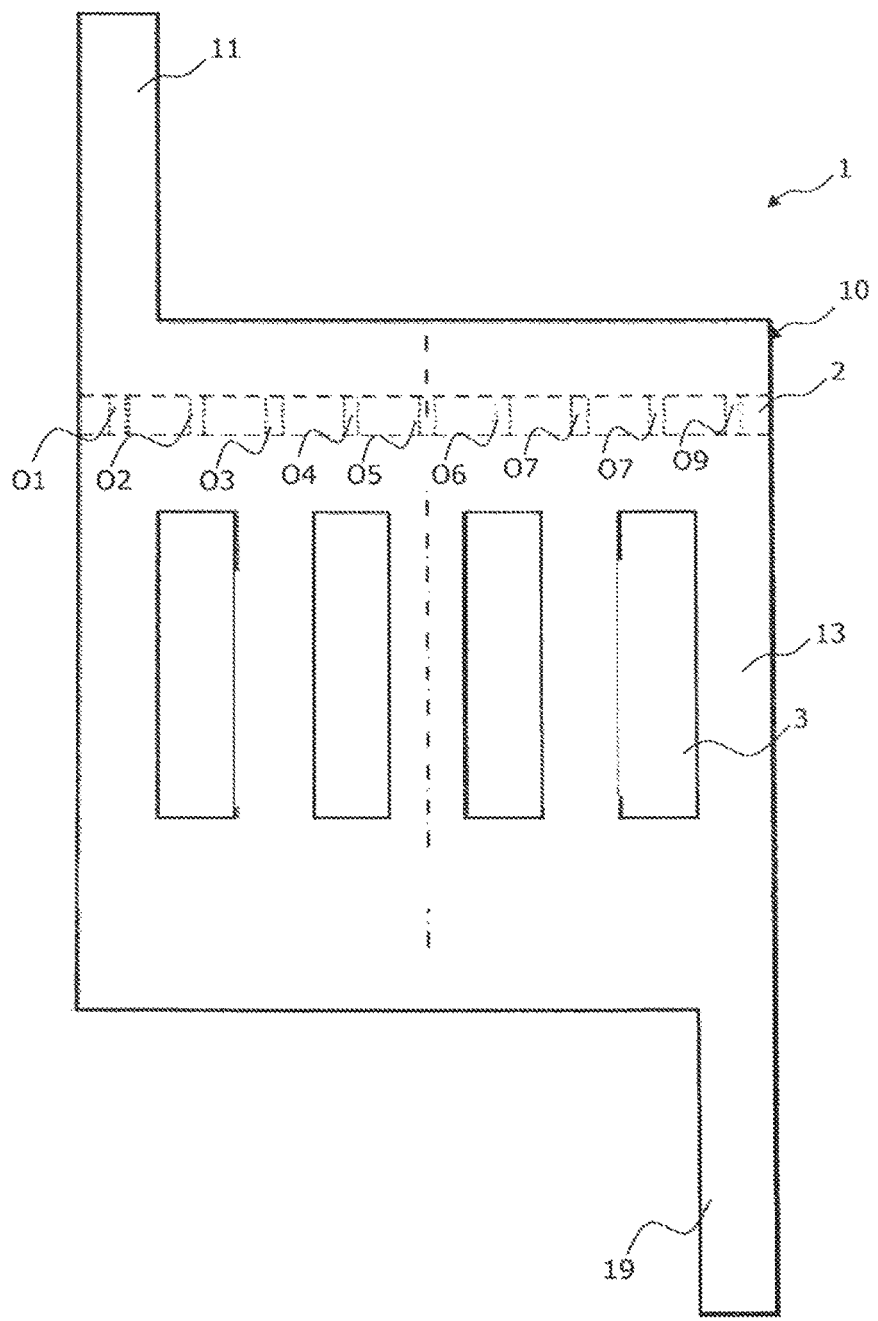
FIG. 2 is a diagrammatic view in two dimensions of a circuit of a heat exchanger across which there is positioned a perforated plate.
Figure 3:
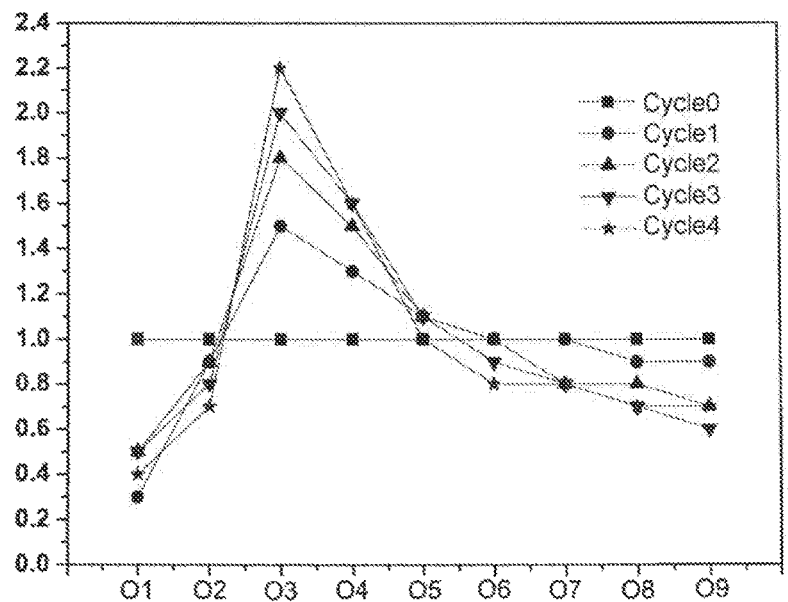
FIG. 3 is a view of a graph plotting up the ordinate axis the ratio of the diameter of each orifice over the mean diameter of the orifices in a plate, e.g. corresponding to the plate of FIG. 2, and along the abscissa axis the references of the corresponding orifices for a series of five calculation cycles marked "Cycle0" to "Cycle4", in accordance with an implementation of the invention.
Figure 4:
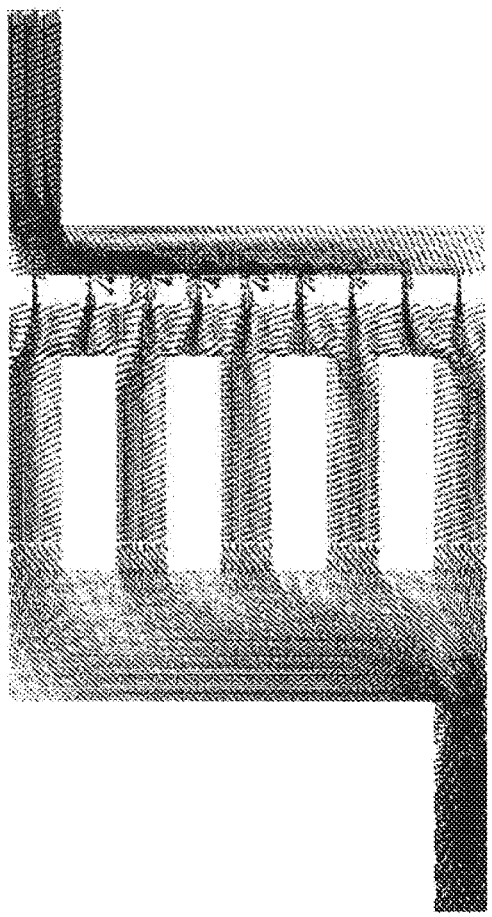
FIG. 4 is an image using point density to show the distribution of speeds in the circuit of the FIG. 3 heat exchanger in which the plate is perforated with orifices of diameters corresponding to the Cycle4 cycle of FIG. 3 or 3A.

Test results are shown in FIGS. 3 to 4 for a method applied in the manner described in detail above for a 2D shape of a heat exchanger as shown in FIG. 2. FIG. 3 shows the diameter values modified for each orifice during the four calculation cycles (or iterations) performed in succession starting from an initial diameter definition corresponding to the curve Cycle0. The graph of FIG. 3 plots up the ordinate axis the ratio $d_i/d_{mean}$ where $d_{mean}$ is the mean diameter of the orifices in the plate, and along the abscissa axis the references of the N orifices, specifically O1 to O9.

Figure 3A:
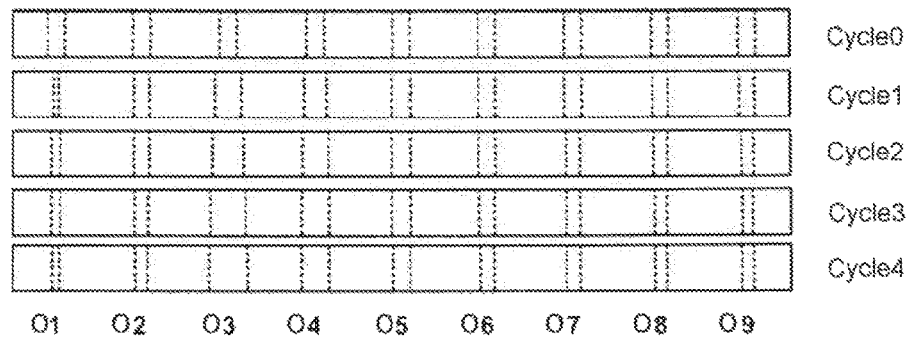
FIG. 3A is a diagrammatic view showing the various diameters of the plate orifices defined in FIG. 3 for the series of five calculation cycles written "Cycle0" to "Cycle4"

FIG. 3A shows the diameters associated with the various orifices in the plate during each cycle Cycle1 to Cycle4 starting from initialization in Cycle0.

Figure 4A:
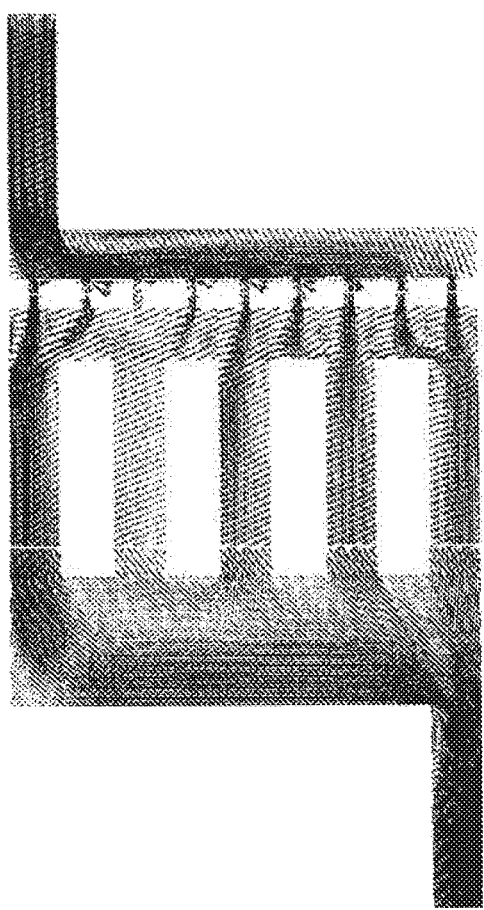
FIG. 4A is an image using point density to show the distribution of speeds in the circuit of the FIG. 3 heat exchanger in which the plate is perforated with orifice diameters corresponding to the Cycle0 cycle of FIG. 3 or 3A.

FIG. 4 serves to visualize the distribution of fluid speeds in the circuit with a plate perforated in compliance with the orifice distribution of the cycle Cycle4. The field of speeds is represented by the density of points it can thus be seen that the distribution of speeds in the five parallel channels in this configuration is more uniform than that which results from the initial distribution of orifice Cycle0, that can be seen in FIG. 4A.

The person skilled in the art can readily understand that the various steps and functions of the implementations described above may be performed in the form of computer programs. In particular, the above-described steps may be performed in the form of electronic and/or computer instructions that are executable by one or more computers.

These computer programs, or computer instructions, may be contained in program storage devices, e.g. in computer-readable digital data storage media, or they may be executable programs. The programs or instructions may also be executed from program storage peripherals.

The present invention is not limited in any way to the implementations described and shown, and the person skilled in the art knows how to apply any variation in accordance with its spirit.

The invention claimed is:

1. A method of determining characteristics of orifices for making through a plate, said plate being for positioning in a circuit across the fluid passage, said method being comprising the steps of:
   a) optionally, defining operational data of the circuit, which data comprises:
   a temperature of a fluid; and/or a pressure of the fluid; and/or a received heat flux; and/or gravity;
   b) defining fluid data, including a flow rate entering the circuit, written Q, and preferably a viscosity, and/or a compressibility, and/or a density of said fluid, as a function of the temperature of the fluid and/or the pressure of the fluid;

c) defining characteristics relating to the orifices, said characteristics comprising:
the number of orifices, written N;
for each orifice:
either a segment referred to as a "control segment" of length;
or an area referred to as a "control area";
each control segment or area corresponding to subdividing at least a portion of the length, of the plate or of the area, of the plate such that the control segments or areas preferably join one another and contain the corresponding orifice;
the diameter, or the area, of the fluid passage of each orifice;
d) meshing said circuit of the plate with the corresponding orifices, together with one or more other elements, if any, present inside said circuit;
e) determining the speed of the fluid stream in a plurality of meshes, preferably in each mesh, as a function of said fluid data, and preferably of said operational data of the circuit;
f) calculating the fluid flow rate $Q_i$ through each orifice in the plate at least as a function of the diameter or of the area of said orifice, and of the determined speed of the fluid stream at said orifice;
g) calculating for each orifice the flow rate density by dividing the fluid flow rate by the length of the control segment or by the control area associated with said orifice, and calculating the mean flow rate density corresponding to the ratio of the incoming flow rate over the length or the area of the plate;
h) determining the optimum or non-optimum nature of the characteristics of the orifices of the plate, by:
for each orifice, comparing the flow rate density with the mean flow rate density; and
if, for each orifice, the difference in absolute value between the flow rate density and the mean flow rate density lies in a predetermined range of values, then the characteristics of the orifices are considered as being optimized; and
otherwise:
modifying at least one of said characteristics of at least some of the orifices;
repeating steps d) to h); and
i) storing a design for said plate incorporating said optimized characteristics of the orifices in a retrievable memory location, said design adapted to fabricate at least one plate having the shape of orifices in accordance with said optimized characteristics.

2. The method according to claim 1, wherein said at least one modified characteristic of at least some of the orifices is the diameter or the area of the fluid passage of the orifice.

3. The method according to claim 2, wherein the diameter of the area of the fluid passage of the orifice is modified to increase the diameter of the orifice if the flow rate density of the orifice is less than the mean flow rate density, and vice versa.

4. The method according to claim 1, wherein said at least one modified characteristic of at least some of the orifices is the number N of orifices.

5. The method according to claim 1, wherein said at least one modified characteristic of at least some of the orifices is the length of the segment or the control area the orifice, without the constraint of being equal to the segment length of the control area of the other orifices.

6. The method according to claim 1, wherein the length of each control segment, or each control area, is defined as being equal to the length of each of the other segments, or equal to each of the other control areas.

7. The method according to claim 1, wherein the step of modifying at least one characteristic of at least some of the orifices is performed while conserving a constant porosity value for the plate, said plate porosity being defined as the sum of the fluid-passing diameters or areas of the orifices divided by the length, or the area, of the plate.

8. The method according to claim 2, wherein the fluid-passing diameter or area of the orifice written or is modified to or in such a manner that:

$$\Delta a_{i,t+1} = \gamma a_{i,t}\left(1 - \frac{Q_{si}}{Q_s}\right)$$

with $\Delta d_{i,t+1} = d_{i,t+1} - d_{i,t}$, and $\gamma$ being a strictly positive real coefficient; or $$\Delta a_{i,t+1} = \gamma a_{i,t}\left(1 - \frac{Q_{si}}{Q_s}\right)$$

with $\Delta a_{i,t+1} = a_{i,t+1} - a_{i,t}$, and $\gamma$ being a strictly positive real coefficient.

9. The method according to claim 1, wherein, for each orifice, the diameter or the fluid passage and the length of the segment or the control area are selected in such a manner that the diameter divided by the length is less than or equal to 1, or the fluid passage divided by the area is less than or equal to 1.

10. The method according to claim 1, wherein the steps d) to h) correspond to a calculation cycle, the method comprising executing a first series of calculation cycles, with a characteristic of at least some of the orifices being modified in step h), and a second series of calculation cycles being executed with another characteristic of at least some of the orifices being modified in step h).

11. The method according to claim 10,
wherein the step of modifying at least one characteristic of at least some of the orifices is performed while conserving a constant porosity value for the plate, said plate porosity being defined as the sum of the fluid-passing diameters or areas of the orifices divided by the length, or the area, of the plate, and
wherein in that each plurality of cycles is performed with a constant value for plate porosity from one cycle to another in the same series, but with a different value for plate porosity from one series to another.

12. The method according to claim 10, wherein the method comprises:
executing a first series of calculation cycles until the defined characteristics of the orifices are considered as being optimized; and
executing the second series of calculation cycles until the defined characteristics of the orifices are considered as being optimized;
for each of said series of calculation cycles, calculating the head loss associated with the orifice characteristics that are considered as being optimized; and
from the orifice characteristics that are considered as being optimized, corresponding to each series of calculation cycles, selecting the series for which the head loss is the smallest.

13. The method according to claim 1, wherein steps d) to h) correspond to a calculation cycle, and a series of calculation cycles is performed with a plate of given shape and/or size, and a second series of calculation is performed with a plate of some other shape and/or size.

14. A non-transitory computer storage device storing program code instructions for executing steps of the method according to claim 1 when said program is executed on a computer.

* * * * *